US00PP29976P2

(12) United States Plant Patent
Verschoor

(10) Patent No.: US PP29,976 P2
(45) Date of Patent: Dec. 11, 2018

(54) ***PHLOX* PLANT NAMED 'VERPRI'**

(50) Latin Name: *Phlox paniculata*
Varietal Denomination: Verpri

(71) Applicant: Janus Verschoor, Haarlem (NL)

(72) Inventor: Janus Verschoor, Haarlem (NL)

(73) Assignee: A. VERSCHOOR HORTICULTURE IMPORT-EXPORT B.V., Haarlem (NL)

( * ) Notice: Subject to any disclaimer, the term of this patent is extended or adjusted under 35 U.S.C. 154(b) by 0 days.

(21) Appl. No.: 15/731,384

(22) Filed: Jun. 5, 2017

(51) Int. Cl.
*A01H 5/02* (2018.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Phlox*, 'Verpri', characterized by its very dwarf and compact plant habit, its floriferous blooming habit with an abundance of flowers, its re-blooming habit, its flowers that are red-purple in color, and its large leaves that are elliptic to narrow elliptic in shape.

2 Drawing Sheets

Botanical classification: *Phlox paniculata.*
Cultivar designation: 'Verpri'.

BACKGROUND OF THE INVENTION

The present invention relates to a new and distinct cultivar of *Phlox paniculata* and will be referred to hereafter by its cultivar name, 'Verpri'. 'Verpri' represents a new herbaceous perennial grown for landscape use.

'Verpri' was selected by the Inventor as a chance seedling in a seedling bed at a nursery in Haarlem, The Netherlands in summer of 2013. The seedling bed had been planted with a mixture of *Phlox paniculata* seed from unknown parents.

Asexual propagation of the new cultivar was first accomplished by stem cuttings by the Inventor in autumn of 2013 in Haarlem, The Netherlands. Asexual propagation by cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Verpri' as a unique cultivar of *Phlox.*

1. 'Verpri' exhibits a very dwarf and compact plant habit.
2. 'Verpri' exhibits a floriferous blooming habit with an abundance of flowers.
3. 'Verpri' exhibits a re-blooming habit.
4. 'Verpri' exhibits flowers that are red-purple in color.
5. 'Verpri' exhibits large leaves that are elliptic to narrow elliptic in shape.

'Verpri' can be most closely compared to the *Phlox paniculata* cultivars 'Rijnstroom' (not patented) and 'Bartwelve' (U.S. Plant Pat. No. 11,804). 'Rijnstroom' differs from 'Verpri' in having fewer flower stems, flowers that are less purple in color, a plant height that is 50% taller, leaves that are oblanceolate in shape and smaller in size, and in lacking a re-blooming habit. 'Bartwelve' differs in having flowers that are more purple in color with a dark red-purple eye, and in having a plant habit that is taller and less broad.

BRIEF DESCRIPTION OF THE DRAWINGS

The accompanying colored photographs illustrate the overall appearance and distinct characteristics of the new *Phlox*. The photographs were taken of a 1 year-old plant of 'Verpri' as field grown in Haarlem, The Netherlands and placed in a 15-cm container for the photographs.

The photograph in FIG. 1 is a view of a plant of 'Verpri' in bloom.

Figure 1:
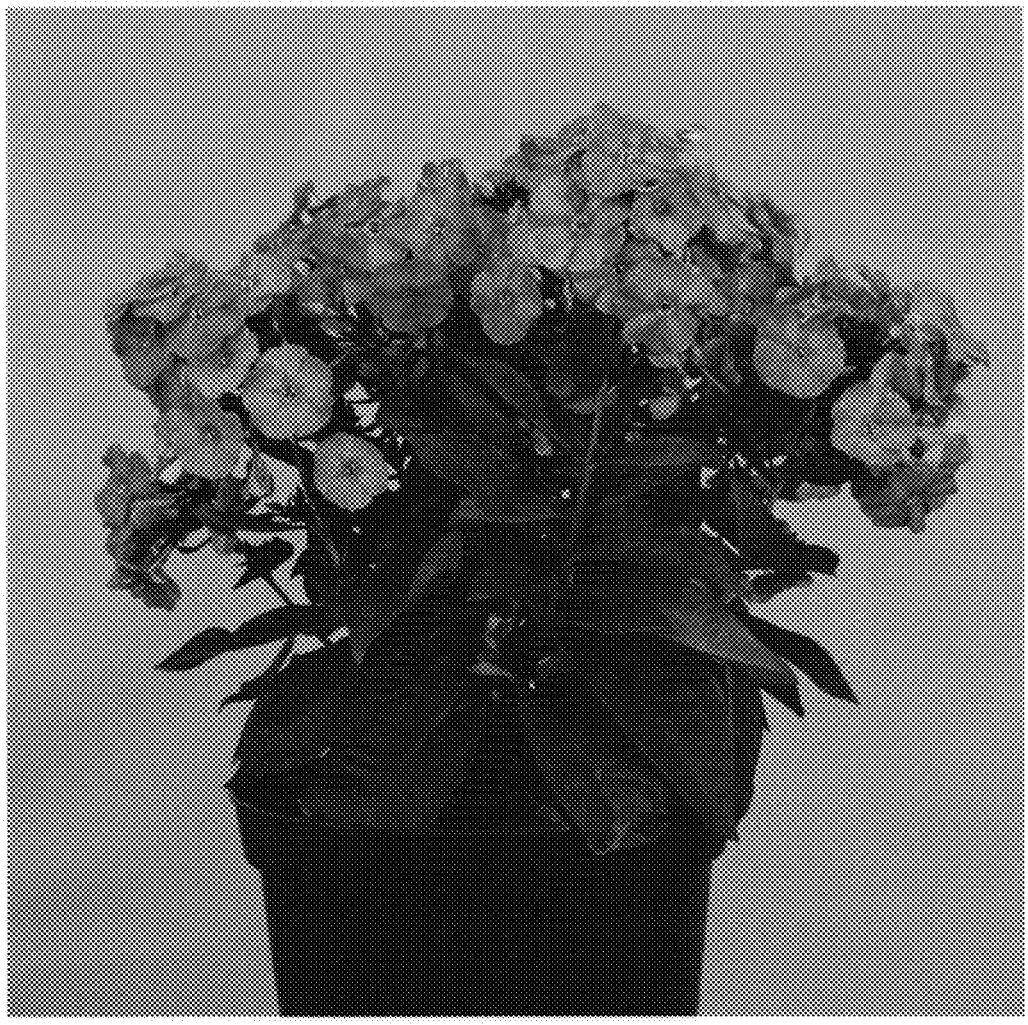
Figure 2:
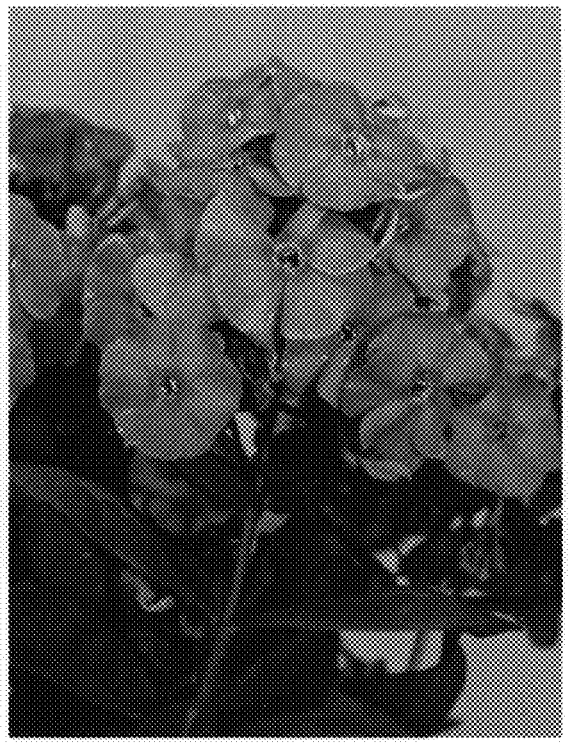

The photograph in FIG. 2 is a close-up view of an inflorescence of 'Verpri'.

Figure 3:
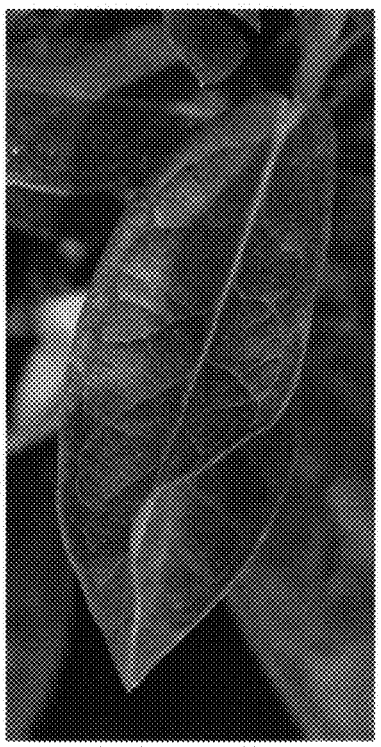

The photograph in FIG. 3 provides a close-up view of a leaf of 'Verpri'.

The colors in the photographs may differ slightly from the color values cited in the detailed botanical description, which accurately describe the colors of the new *Phlox.*

DETAILED BOTANICAL DESCRIPTION OF THE PLANT

The following is a detailed description of 1 year-old plants of the new cultivar as field grown in Haarlem, The Netherlands. The plants were grown under average day temperatures of 15° C. to 30° C. and average night temperatures of 12° C. to 20° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Mid June and re-blooming into September in the Netherlands.

*Plant type*.—Herbaceous perennial.
*Plant habit*.—Broad upright.
*Height and spread*.—Reaches an average of 35.5 cm in height (including inflorescences) and about 46.6 cm in spread.
*Hardiness*.—At least in U.S.D.A. Zones 6 to 10.
*Diseases*.—No resistance or susceptibility has been observed.
*Root description*.—Fibrous.
*Growth rate*.—Moderately vigorous.
*Propagation*.—Stem cuttings, root cuttings, and tissue culture.
*Root initiation*.—About 30 days in summer.
*Root development*.—Average of 30 weeks to fully develop in a liner as a young plant.

Stem description:
*Stem quantity*.—Average of 8 main branches and 2 lateral branches per main stem.
*Stem size*.—18.2 cm in length (excluding inflorescence), average of 4 mm in diameter.
*Stem shape*.—Round.
*Stem strength*.—Strong.
*Stem color*.—145B.
*Stem surface*.—Slightly glossy.
*Stem aspect*.—Held in an average angle of 35° to soil level (=0°).
*Internode length*.—An average of 2.2 cm.
*Branching habit*.—Main stems grow from the base with lateral stems present.

Foliage description:
*Leaf shape*.—Elliptic to narrow elliptic.
*Leaf division*.—Simple.
*Leaf base*.—Truncate.
*Leaf apex*.—Acute.
*Leaf venation*.—Pinnate, color upper side 144A, color lower side 144B.
*Leaf margins*.—Entire, finely serrate.
*Leaf attachment*.—Petiolate.
*Leaf arrangement*.—Opposite.
*Leaf surface*.—Both surfaces are very slightly rugose and very slightly glossy.
*Leaf color*.—Young upper surface; 143A, young lower surface; 146C, mature upper surface; between NN137A and 147A, mature lower surface; between 146B and 147B.
*Leaf size*.—An average of 11.4 cm in length and 4.3 cm in width.
*Leaf quantity*.—An average of 20 (10 pairs) per stem.
*Petioles*.—Flattened, an average of 2.5 mm in width, 2 mm in height and 4 mm in length, upper surface 144B in color, lower surface 144B to 144C in color, both surfaces are smooth, glabrous and matte.

Flower description:
*Inflorescence type*.—Compound terminal panicle.
*Lastingness of inflorescence*.—Individual flowers lasts about 10 days, 3 to 4 weeks per inflorescence, inflorescences are continuously produced during the bloom season.
*Inflorescence size*.—An average of 11.1 cm in height and 11.6 cm in diameter.
*Flower fragrance*.—Moderate, sweet and pleasant *phlox* fragrance.
*Flower number*.—Average of 110 per inflorescence.
*Flower aspect*.—Outward to upright.
*Flower bud*.—An average of 1.9 cm in length and up to 6 mm in diameter, oblanceolate in shape, color; between 70B and 72B, immature tube 145B to 145C, tinged N77B, immature calyx 145B to 145C, strongly tinged 203B.
*Flower form*.—Salverform.
*Flower size*.—An average of 3.8 cm in height and diameter, 2.7 cm in length, throat diameter 5 mm, tube length 2.1 cm, tube diameter 3 mm.
*Petals*.—5, 1 whorl, strongly overlapping, self-cleaning, both surfaces are glabrous, smooth and velvety, throat surfaces are glabrous and smooth, tube surfaces are moderately covered with very short soft hairs, average of 0.2 mm in length and too small to measure color, rotate and moderately overlapping arrangement, petals are fused 57% into tube, spathulate in shape, margins entire, apex obtuse to broad emarginate, average of 3.7 cm in length, 2.2 cm in width, color when opening upper side; between N74A and NN74A, color when opening lower side; N74C to NN74C to NN74D, color when fully open upper surface; N74A to N74B, color when fully open lower surface; N74C to N75C to N75D, color on upper surface fading to NN74B, throat surface and vein color N74A, tube surface and vein color 75A to 75B.
*Calyx*.—Rotate in form, an average of 9 mm in length and 5 mm in diameter.
*Sepals*.—5, 1 whorl, base lower 11% fused, narrow lanceolate in shape, margins entire, apex narrowly apiculate in shape, an average of 9 mm in length and 2 mm in width, both surfaces are glabrous, smooth and matte, color; when opening upper surface 144D, tinged 203B, when opening lower surface 145B to 145C, tinged 203B, when fully open upper surface 144D, tinged 203B, when fully open lower surface 145B to 145C, tinged 203B.
*Peduncles*.—Oval in shape, strong, 7.4 cm in length, 2 mm in diameter, vertical angle, smooth, glabrous and slightly glossy surface, 144B in color.
*Pedicels*.—Oval in shape, moderately strong, an average of 6 mm in length and 0.8 mm in diameter, average of 60° angle, smooth, glabrous and matte surface, 145B in color.

Reproductive organs:
*Gynoecium*.—Pistil; 1, 1.8 cm in length, stigma; cleft (3-parted), 150D in color, 2 mm in diameter, style; 1.7 cm in length, N77B in color, ovary; 143B in color.
*Androcoecium*.—Stamens; 5, anthers; basifixed and oblong in shape, 2 mm in length, 0.5 mm in width, 158C to 158D in color, filaments; 1 mm in length, 76D in color, pollen is moderate in quantity and 11D in color.
*Seeds*.—None observed to date.

It is claimed:

1. A new and distinct cultivar of *Phlox* plant named 'Verpri' as herein illustrated and described.

* * * * *